US00PP08712P

United States Patent [19]

Schumann

[11] Patent Number: Plant 8,712

[45] Date of Patent: May 3, 1994

[54] GERANIUM PLANT NAMED FISBLURI

[75] Inventor: Ingeborg Schumann, Albstadt, Fed. Rep. of Germany

[73] Assignee: Florfis AG, Binningen, Switzerland

[21] Appl. No.: 94,328

[22] Filed: Jul. 21, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Foley & Lardner

[57] ABSTRACT

A new and distinct cultivar of geranium named Fisbluri, particularly characterized by the combined features of purple pink flower color, medium to dark foliage with weak zonation, medium to vigorous growth habit, comparatively early spring flower, and large umbels.

1 Drawing Sheet

The present invention comprises a new and distinct cultivar of geranium, botanically known as *Pelargonium zonale L'hert,* and hereinafter referred to by the cultivar name Fisbluri.

Fisbluri was originated from a hybridization made by the inventor Ingeborg Schumann in a controlled breeding program in Galdar, Gran Canaria, Spain in 1987. The female parent was hybrid produced by crossing a self seedling of Rospen and a plant of the cultivar Blues, disclosed in U.S. Plant Pat. No. 5,373, variety Blues. Rospen is characterized by purple pink semi-double flowers with red and white maculas on the petals. Blues has pink flowers with similar markings. Both varieties have medium green foliage. The male parent of Fisbluri was Fisrix, characterized by single pink flowers with purple eyes, and dark green foliage.

Fisbluri was discovered and selected as one flowering plant within the progeny of the stated cross by Ingeborg Schumann in 1988 in a controlled environment in Galdar, Gran Canaria, Spain.

The first act of asexual reproduction of Fisbluri was accomplished when vegetative cuttings were taken from the initial selection in February 1989 in a controlled environment in Galdar, Gran Canaria, Spain, by, or under the supervision of, Ingeborg Schumann.

Horticultural examination of plants grown from these cuttings initiated in May 1989 in Hillscheid, Federal Republic of Germany, and continuing thereafter, has demonstrated that the combination of characteristics as herein disclosed for Fisbluri are firmly fixed and are retained through successive generations of asexual reproduction.

Fisbluri has not been observed under all possible environmental conditions. The phenotype may vary significantly with variations in environment such as temperature, light intensity and day length, without, however, any variation in genotype. The following observations measurements, and comparisons describe plants grown in Hillscheid, Federal Republic of Germany under greenhouse conditions which approximate those generally used in commercial practice.

The following traits have been repeatedly observed and are determined to be basic characteristics of Fisbluri, which in combination distinguish this geranium as a new and distinct cultivar:

1. Purple pink semi-double flowers with purple and white markings
2. Medium to dark green foliage with weak zonation
3. Medium to large plant habit 4. Early spring flower response for a dark leafed cultivar
5. Very broad umbels, semi-spherically shaped Of the many commercial cultivars known to the present inventor, there is no cultivar with which Fisbluri closely compares. The flower color of Fisbluri is between Rospen and Blues, and Fisbluri has dark green foliage in contrast to Rospen and Blues.

The accompanying color photographic drawing shows typical flower and foliage characteristics of Fisbluri, with colors being as true as possible with illustrations of this type.

In the following description color references are made to The Royal Horticultural Society Colour Chart. The color values were determined indoors from plants grown indoors in Hillscheid, Federal Republic of Germany.

Classification:

*Botanical.*—A hybrid of the species *Pelargonium zonale L'hert.*

*Commercial.*—Zonal geranium, cv., Fisbluri.

INFLUORESCENCE

A. Umbel:

*Shape.*—Semi-spherical.
*Average diameter.*—125 mm.
*Average depth.*—55 mm.
*Peduncle length.*—190 mm.
*Peduncle color.*—Green and dark red.
*Pedicel length.*—30 mm.
*Pedicel color.*—Dark Red.

B. Corolla:

*Average diameter.*—49 mm.
*Form.*—Semi-double.
*Number of petals.*—6–9.
*Number of petaloids.*—1–3.
*Color (general tonality from a distance of three meters).*—Bluish pink.
*Color of upper petals.*—57C.
*Color of lower petals.*—66D.
*Markings on upper petals.*—Purple eyes (57A) and white base.
*Markings on lower petals.*—Weak purple eyes.
*Color of lower surface of petals.*—68 A/B with veins.
*Color of sepals.*—Green, red at base.
*Number of sepals.*—5–7.

C. Bud:

*Shape.*—Elliptic.

*Color (adaxial).*—Green, with weak anthocyanin at the base.

*Color (abaxial).*—Pink.

D. Reproductive organs:

*Androecium.*—5-11 fertile anthers, white filaments, orange pollen.

*Gynoecium.*—5-6 lobed stigma, dark red style and stigma.

E. Spring flowering response period: In Hillscheid, Federal Republic of Germany, in 1993 plants had on average 0.9 flowers opened 13 weeks after planting of unrooted cuttings.

F. Outdoor flower production: The flower count in 1992 in Hillscheid, Federal Republic of Germany was between 30 and 35 flowers per plant for May through August observation period.

G. Durability: Shatter resistance good.

PLANT

A. Foliage:

*Form.*—Kidney-shaped.

*Margin.*—Bicrenate.

*Color of upper surface.*—Medium to dark green, approximately 137B.

*Color of zonation.*—Darker green, 137A.

*Size of leaf.*—Up to 100 mm.

*Tolerance of botrytis.*—Average.

B. General appearance and form:

*Internode length.*—3.4 cm.

*Branching pattern.*—2.8 branches per week.

*Height (13 week old plants).*—19 cm.

I claim:

1. A new and distinct cultivar of geranium plant named Fisbluri, as illustrated and described.

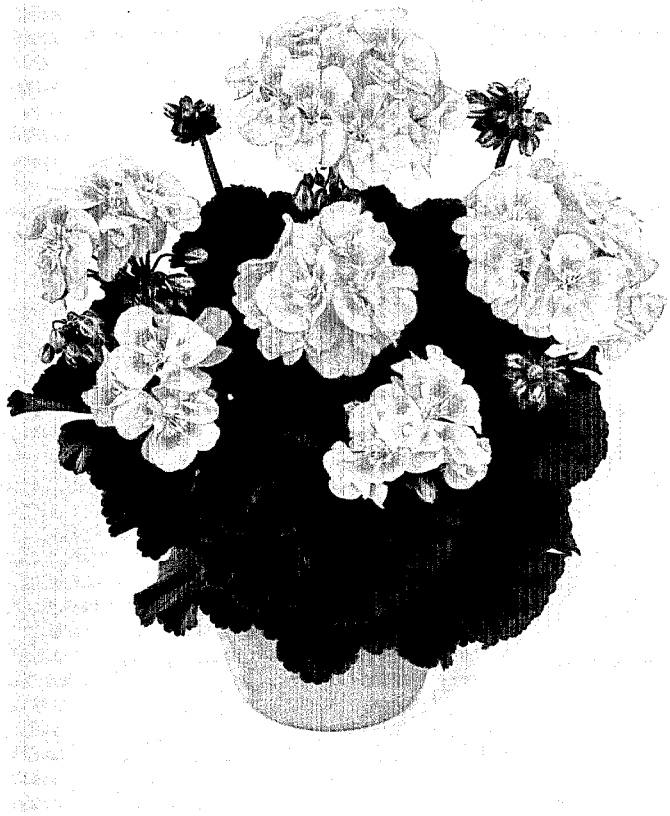

* * * * *